United States Patent [19]

Yoo

[11] 3,989,759

[45] Nov. 2, 1976

[54] HYDROFORMYLATION PROCESS OVER CATALYST HAVING SILICA ALUMINA SUPPORT WITH SEPARATE ALUMINA PHASE AND NOBLE METAL AND COBALT OR NICKEL

[75] Inventor: Jin Sun Yoo, South Holland, Ill.

[73] Assignee: Atlantic Richfield Company, Los Angeles, Calif.

[22] Filed: Feb. 18, 1975

[21] Appl. No.: 550,247

Related U.S. Application Data

[63] Continuation of Ser. No. 51,659, July 1, 1970, abandoned.

[52] U.S. Cl. .......................................... 260/604 HF
[51] Int. Cl.² ........................................ C07C 45/08
[58] Field of Search ............................. 260/604 HF

[56] References Cited
UNITED STATES PATENTS 3,352,924   11/1967   Gladrow et al. .............. 260/604 HF
3,576,881   4/1971   Senn ............................ 260/604 HF

FOREIGN PATENTS OR APPLICATIONS 801,734   9/1958   United Kingdom .......... 260/604 HF

OTHER PUBLICATIONS

Tucci, E. R., I & E.C. Product Res. & Dev., vol. 7, 1968, pp. 32–38.

Primary Examiner—James O. Thomas, Jr.
Assistant Examiner—W. B. Lone
Attorney, Agent, or Firm—John R. Ewbank

[57] ABSTRACT

A new solid catalyst suitable for the hydroformylation including hydroxyhydroformylation, of low molecular weight olefins is disclosed. The catalyst composition is a hydrido-cobalt or nickel-carbonyl-Group VA electron donor ligand-platinum-group metal complex on a solid, porous, acidic, silica-based support.

5 Claims, No Drawings

HYDROFORMYLATION PROCESS OVER CATALYST HAVING SILICA ALUMINA SUPPORT WITH SEPARATE ALUMINA PHASE AND NOBLE METAL AND COBALT OR NICKEL

RELATED CASES

This is a continuation of Ser. No. 51,659 filed July 1, 1970, now abandoned. A related application, Ser. No. 20,422 filed Mar. 17, 1970 was abandoned by the filing of its continuation Ser. No. 522,008 on Feb. 24, 1975.

FIELD OF INVENTION

This invention relates to a new solid catalyst composition suitable for the hydroformylation, including hydroxyhydroformylation, of low molecular weight olefins to form aldehydes and alcohols. This invention relates also to an improved hydroformylation process conducted in the presence of the novel solid catalyst.

SUMMARY OF INVENTION

In copending application Serial No. 20,422 [(Attorney's Docket No. 1-2859A)], filed Mar. 17, 1970, in the name of Jin Sun Yoo, there is disclosed a catalyst composition suitable for the hydroformylation, including hydroxyhydroformylation, of low molecular weight olefins. As disclosed therein, the catalyst composition is a hydrido-cobalt or nickel-carbonyl-Group VA electron donor ligand on a solid, acidic, silica-based support material. The aforesaid application discloses this hetrogeneous catalyst system and further shows the advantages of this catalyst system in the hydroformylation of low molecular weight olefins. It has now been found that the addition of a platinum-group metal (e.g., platinum, palladium, rhodium, ruthenium, osmium and iridium) promoter to this catalyst system enables the hydroformylation process to be conducted at substantially lower temperatures and lower pressures for a given olefin feed conversion. In particular, it has been found that the addition of a platinum-group metal to the solid catalyst system enables the hydroformylation process to be conducted at temperatures about 40° to 60° C. lower than the system without the platinum-group metal promoter. Thus, a low temperature hydroformylation process is now feasible using the catalyst system of this invention. The catalyst-forming reactants can be combined in a molar ratio of electron donor ligand to cobalt or nickel of about 1 to 4:1, preferably about 1.5 to 3:1, although either the metal or the ligand, preferably the ligand, can be present in excess. The cobalt or nickel and electron donor ligand are present on the support in minor, catalytically-effective amounts while the support is the major part of the catalyst. The metal and silica-based support can be present in amounts sufficient to yield an amount of cobalt or nickel, based on the support, of about 0.05 to 1 weight percent, preferably 0.2 to 0.6 weight percent. The platinum-group metal promoter catalyst can be present in a minor amount sufficient to catalytically promote the hydroformylation reaction of low molecular olefins at low temperature, which amount can be, for example, from about 0.002 to 0.05 weight percent, based on the support, preferably about 0.01 to 0.03 weight percent.

In the preparation of the catalyst composition of the present invention, the platinum-group metal source is provided by compounds which are slightly soluble in some solvent wherein the cobalt- or nickel-Group VA ligand complex can be formed. Preferred are the weak field platinum-group metal complexes, the ligands of which readily served in solution as transfer agents. Suitable sources of the platinum-group metal include, for example, halides, e.g. $MX_m^{n-}$ ($n= 0,2$; $m= 3, 4, 6$) where M represents a platinum-group metal; dihydrocarbyloxy metal derivatives, i.e. $M(OR)_2$ where R represents alkyl, aryl, alkaryl and the like groups; dihydrocarbyloxy metal carboxylates, i.e., $(RO)_2MOOCR'$ where R and R; are as defined above as R; diphosphine complexes, e.g. $(M[(C_6H_5)_2PC_2H_4P(C_6H_5)_2]X_2$, where X is a halide. Also available as platinum-group metal sources are chelates formed by the platinum-group metal and weak field ligands, such as $\beta$-diketones or $\beta$-ketocarboxylic acid esters and salts and carboxylic acids. Examples of these types of platinum-group metal sources include $\beta$-diketonato M(II), acetylacetonato M(II), propylacetonato M(II), benzoacetonato M; chelates from $\beta$-ketocarboxylic acid esters; salts of saturated monocarboxylic acid, e.g. the platinum-group metal formate, propionate, octoate, palmitate, stearate, phenol acetate, phenol propionate, and the like; salts of corresponding saturated monocarboxylic acids, e.g. the platinum-group metal acrylate, vinyl acetate, and the like; salts of saturated dicarboxylic acids, e.g. the platinum-group metal adipate, decane-1, 10-dicarboxylate, and the like; salts of corresponding unsaturated dicarboxylic acids, e.g. the platinum-group metal muconate and the like; salts of cyclic and aromatic carboxylic acids, e.g. platinum-group metal cyclohexane carboxylate, benzoate, phthalates and the like; and dialkoxycarbolates, e.g. platinum-group metal dimethoxy acetate and the like. Suitable sources of the platinum-group metal thus include palladium acetylacetonate, palladium naphthenate, platinum acetylacetone, rhodium naphthenate, rhodium chloride, ruthenium chloride, osmium acetylacetonate, iridium naphthenate, and the like. The preferred platinum-group metal is palladium and the prefered palladium source is palladium acetylacetonate.

The cobalt or nickel source is also provided by the compounds of the metals which are at least slightly soluble in some solvent wherein the metal-Group VA ligand complex can be formed. The preferred sources are thus the nickel or cobalt compounds corresponding to the palladium compounds listed above.

The electron donor ligand component employed in preparing the metal complex component of the catalyst of the present invention is preferably a triorganoamine or a triorganophosphine corresponding to the general formulas $R_3N$ or $R_3P$ wherein R is a hydrocarbon radical, e.g. alkyl, aryl, alkaryl, aralkyl and cycloalkyl, of from 1 to about 20 carbon atoms, preferably 2 to about 6 carbon atoms and devoid of olefinic or acetylenic unsaturation. Different R groups may, of course, be present in the same molecule. When the phosphine component contains aromatic groups it is generally preferred that these have mono-cyclic structures, e.g., that the groups be selected from phenyl, alkylphenyl, or phenylalkyl radicals.

Multifunctional phosphines of the formula $R_2P-(CH_2)_n-PR_2$ such as bis(diphenylphosphine)ethane, may be used in place of the foregoing described unidentate phosphines. Phosphines may also be replaced by other electron donor ligands such as, for example, alkyl, aryl, alkaryl, aralkyl, or cycloalkyl phosphites, arsines, stilbines or bismuthines. Other monodentate or bidentate ligands containing nitrogen donating centers such as pyridine or alpha, alpha-bipyridyl, may also be utilized. It is, however, preferred that triorganophosphines be utilized. Examples of suitable phosphines for the composition of the present invention are triphenylphosphine, trimethylphosphine, tricyclohexylphosphine, tri-n-hexylphosphine, tri-n-decylphosphine, tribenzylphosphine, tri-(4-n-butylphenyl)phosphine, and the like. Generally speaking, the electron donor ligand compounds of Group VA elements of the periodic table, having atomic numbers of 7 to 83 can be used in the catalysts.

The solid support of the catalyst of the present invention can be an acidic, silica-based material, e.g., having a D + L activity of at least about 20, preferably at least about 30 when determined according to the method of Birkhimer et al., "A Bench Scale Test Method for Evaluating Cracking Catalysts", Proceedings of the American Petroleum Institute, Division of Refining, Vol. 27 (III), page 90 (1947), and hereinafter referred to as Cat. A. The silica-based support preferably has a substantial surface area as determined by the BET nitrogen absorption procedure (JACS, Vol. 60, pp. 309 et seq.) (1938). The surface area of the support can be at least about 50 square meters per gram, and such surface areas are often up to about 500 or more $m^2/gm.$, preferably about 150 to 400 $m^2/gm$. It is preferred that the catalyst support be relatively dry to avoid undue reaction with and loss of catalytic promoting materials. Thus, it is advantageous that the support be calcined, e.g., at temperatures of about 600° to 1500° F., or more, to reduce the water content, but such calcination should not be so severe that the support is no longer catalytically-active.

The support component contains other materials in addition to silica which materials, when combined with silica, provide an acidic material as in, for instance, the case of silica-alumina. Often these materials are one or more oxides of the metals of Groups II, III and IV of the Periodic Table. Examples of the composites contemplated herein under the generic designation of silica-based materials are often composed predominantly of, or even to a major extent of, silica. These supports include, for example, silica-alumina, silica-boria, silica-zirconia, silica-magnesia, silica-alumina-zirconia, silica-alumina-thoria, silica-alumina-magnesia, and the like. The silica-based support can contain amorphous or crystalline material such as crystalline aluminosilicate, for instance, having pore openings in the 6 to 15 Angstrom unit range. The support often contains silica and alumina and such supports, whether naturally-occurring as in acid-treated clays, or a synthetic gel, will frequently contain about 10 to 60, preferably about 15 to 45, weight percent alumina. In addition, such silica-alumina supports can, and preferably do, contain a portion of the alumina as a separate, distinct phase.

A highly preferred catalyst support can be made by combining a silica-alumina hydrogel with a hydrous alumina with or without (preferably without) a crystalline aluminosilicate. An advantageous hydrous alumina component is, when analyzed by X-ray diffraction of dry samples, either one or a mixture of amorphous hydrous alumina and a monohydrate, e.g., boehmite, of less than about 50 A, preferably less than about 40 A, crystalline size as determined by half-width measurements of the (0, 4, 1) X-ray diffraction line calculated by the Debye-Scherrer equation. The mixture of the catalyst precursor components can be dried, e.g., at about 220° to 500° F. to convert the silica-alumina hydrogel to xerogel form. The dried material can then be calcined, e.g., at a temperature of about 700° to 1500° F., preferably about 800° to 1400° F., to provide the active catalyst support. During calcination, the separate hydrous alumina phase of the mixture is converted to a gamma form or other catalytically-active alumina.

In providing the preferred catalyst support precursor for drying, the components can be combined in any suitable manner or order desired, and advantageously each of the components is in the mixture in finely-divided form, preferably the particles are principally less than about 300 mesh in size. The finely-divided material can have an average particle size of about 10 to 150 microns and can be used to make a catalyst of this particle size which can be employed in a fluidized bed type of operation. However, if desired, the mixture of catalyst support components can be placed in macrosized form, that is, made into particles as by tabletting, extruding, etc., to sizes of the order of about 1/64 inch to ½ inch or more in diameter and about 1/32 inch to 1 inch or more in length, before or after drying or calcination. If formation of the macrosized particles is subsequent to calcination and the calcined particles have been contacted with water, the material can be recalcined.

On a dry basis, the preferred supports of the catalysts of the present invention contain about 45 to 95 weight percent of the amorphous silica-alumina xerogel, about 5 to 55 weight percent of the separately added alumina phase, and about 0 to 50 weight percent of the crystalline aluminosilicate, preferably the proportions of these ingredients are about 75 to 90%, about 10 to 25% and about 0 to 20%, respectively. If present, the crystalline aluminosilicate is usually at least about 1 weight percent, preferably at least about 5 weight percent, based on the dried support. The alumina content from the silica-alumina xerogel and the separate alumina phase is about 20 to 70 weight percent, preferably about 25 to 60 weight percent, based on the dried support. Also, the catalyst support generally contains less than about 1.5 weight percent, preferably less than about 0.5 weight percent, sodium.

The silica-alumina component of the precursor of the preferred catalyst support of the present invention can be a silica-alumina hydrogel which contains about 55 to 90, preferably 65 to 75, weight percent silica and about 10 to 45, preferably about 25 to 35, weight percent alumina, on a dry basis. The silica-alumina can be naturally-occurring or can be synthetically prepared by any desired method and several procedures are known in the art. For instance, an amorphous silica-alumina hydrogen can be prepared by co-precipitation or sequential precipitation by either component being the initial material with at least the principal part of the silica or alumina being made in the presence of the other. Generally, the alumina is precipitated in the presence of a silica gel. It is preferred that the silica-alumina hydrogel be made by forming a silica hydrogel by precipitation from an alkali metal silicate solution and an acid such as sulfuric acid. Then alum solution may be added to the silica hydrogel slurry. The alumina is then precipitated by raising the pH into the alkaline range by the addition of an aqueous sodium aluminate solution or by the addition of a base such as ammonium hydroxide. Other techniques for preparing the silica-alumina hydrogel are well known in the art, and these techniques may be used in the practice of the invention.

The alumina hydrogel which can be combined with the silica-alumina is made separately from the silica-alumina. The alumina hydrogel may be prepared, for example, by precipitation of alumina at alkaline pH by mixing alum with sodium aluminate in an aqueous solution or with a base such as soda ash, ammonia, etc. As noted above, the alumina hydrogel can be in the form of amorphous hydrous alumina or alumina monohydrate, e.g., of up to about 50 A crystallite size as determined by X-ray diffraction analysis. The amorphous hydrous alumina generally contains as much combined water as does an alumina monohydrate. Mixtures of the monohydrate and amorphous forms of hydrous alumina are preferred and often this phase is composed of at least about 25% of each of the separate members.

In preparing the catalyst support, one may separately filter the silica-alumina hydrogel and the hydrous alumina and intimately mix these materials, for instance, by colloidal milling. Although in this particular procedure a low sodium crystalline aluminosiliate can be added after the milling, this ingredient can also be combined before the colloidal milling operation. The mixture is dried, water-washed to acceptable concentrations of, for instance, sodium, and redried in the preferred procedure. The drying, especially the initial drying, is advantageously effected by spray drying to give microspheres.

The crystalline aluminosilicate which can be present in the silica-based catalyst support of the present invention, can have pore openings of 6 to 15 A in diameter, and preferably the pore openings have a diameter of 10 to 14 A. Usually, with a given material, the pores are relatively uniform in size and often the crystalline aluminosilicate particles are primarily less than about 15 microns in size, preferably less than about 10 microns. In the crystalline aluminosilicate the silica-to-alumina mole ratio is often greater than about 2:1 and is usually not above about 12:1, preferably being about 4 to 6:1. The aluminosilicate may be available in the sodium form, and the sodium can be removed before or after the crystalline aluminosilicate is added to the other catalyst support ingredients.

It is preferred to exchange the sodium with ammonium ions, for instance, through contact with an aqueous solution of ammonium chloride or another water-soluble ammonium compound. Subsequently, during drying and/or calcination, the ammonium ion may break down to release ammonia and leave an acid site on the aluminosilicate. On a molar basis, the ammonium or hydrogen ion is usually at least about 10% or even at least about 50%, based on the alumina content of the crystalline aluminosilicate. Suitable replacements for the sodium also include the polyvalent metals of the periodic chart, including the Group II-a and rare earth metals such as cerium, etc. The metals may be present along with the ammonium or hydrogen cations.

The preparation of the overall catalyst composition is preferably conducted by first forming the complex of the electron donor ligand, the platinum-group metal source and the cobalt or nickel source. For illustration purposes, formation of the overall catalyst composition will be described in terms of cobalt and palladium, although it is understood that the nickel and other platinum-group metal catalyst compositions can be formed in the same manner. The cobalt source and ligand an be present in about the stoichiometric amounts necessary to form the complex or one component can be present in an excess amount of that necessary for the formation of the complex.

Formation of the ligand-cobalt-palladium complex may be effected by simply mixing the three reactants in the presence of a suitable solvent for the complex reaction. The mixing may be done at room temperature or up to as high as about 300° F. The complex usually forms within about 20 to 40 minutes after mixing at elevated temperature. Suitably solvents for the complex-forming reaction include the same solvents which are suitable for use in the final catalyst composition. If desired, however, the complexing may be accomplished in a solvent which is unsuitable for use in the final composition; in this case the resultant complex will first be isolated from the reaction mixture and redissolved, or re-suspended, in a proper solvent which is inert to the final catalyst composition.

Thus, for example, one method of preparing the phosphine-cobalt and palladium complexes can involve stirring, preferably at room temperature, a mixture of the tri-n-butylphosphine, cobalt acetylacetonate and palladium acetylacetonate, preferably at a temperature of about 150° to 250° F., and isolating the resultant complex from the reactant mixture. This approach is often preferred where the metal reagents contain some water of hydration, as the water will be removed from the complex when the latter is separated from the alcohol solvent.

In either case, the cobalt and palladium-triorgano phosphine complexes can be dissolved in a suitable solvent, e.g., ethanol, methanol, benzene, chlorobenzene, or the like, and charged to a reactor. Hydrogen and carbon monoxide gas can then be introduced separately, or as a premixed gas, in a molar ratio of hydrogen to carbon monoxide of from about 1:1 to 5:1, preferably from about 1.2:1 to 3.5:1, at a temperature of from about 60 to 400° C., preferably from about 100° to 250° C., and a pressure of from about 500 to 3000 psig., preferably from about 700 to 1800 psig. to obtain the hydrido-cobalt carbonyl-triorgano phosphine and palladium complexes. The solid support, in finely-divided form, is added to the complex in the solvent and the system is agitated for a time sufficient to affix the complex on the support.

The solid supported catalyst can also be prepared in situ by charging the metal sources, such as cobalt acetylacetonates and palladium acetylacetonate, the electron donor ligand, such as tributyl phosphine or triphenyl phosphine, and the support in finely-divided form in a suitable solvent to an autoclave reactor and allowing these components to react under a premixed gas of hydrogen and carbon monoxide of a molar ratio of hydrogen to carbon monoxide of from about 1:1 to 5:1 at a pressure of from about 500 to 3000, preferably 700 to 1800, psig., and a temperature of from about 100° to 195° C. for about one hour. The resulting supported catalyst system can be separated by removing the liquid phase from the reactor. If desired, the low molecular weight olefin can be charged to the catalyst system before separation and the hydroformylation reaction carried out in the presence of the solvent. After the reaction is completed, the liquid reaction mixture can be separated and removed from the reactor. Alternatively, the catalyst components, support and low molecular weight olefin can be charged simultaneously in a solvent to the autoclave under conditions as set forth above, thus allowing the system to simultaneously undergo formation of the solid supported catalyst system and the hydroformylation of the low molecular weight olefin.

The solid supported catalyst system can also be prepared by dissolving the metal sources such as cobalt naphthenate or cobalt acetylacetonate and palladium naphthenate or palladium acetylacetonate in a solvent such as benzene or alcohol. The solid support is added to the resulting pink solution and the system is agitated at room temperature overnight yielding a colorless supernatent liquid and pinkish-colored support particles. These cobalt-palladium-impregnated support particles are then filtered, washed and dried in an oven. The dried cobalt-palladium-impregnated particles are charged to a reactor along with an electron donor ligand, such as tributyl phosphine, in a solvent. The system is pressured with hydrogen and carbon monoxide under conditions as set forth above for in situ preparation and the hydrido-cobalt carbonyltriorgano phosphine and palladium complex on a solid, acidic, silica-based support catalyst recovered. An olefin feed can be introduced with the hydrogen and carbon monoxide also in the manner set forth above for in situ preparation.

The supported catalyst composition of the present invention is effective for hydroformylation, including hydroxyhydroformylation, of olefinic hydrocarbons, e.g., of 2 to about 16 carbon atoms, preferably 3 to 10 carbon atoms, and is highly desirable for such uses. For example, it is possible to provide alcohols, aldehydes, and the like from aliphatic mono-olefins. Of particular interest, however, is the selective activity of the present catalyst composition in the hydroformylation of pentene to form hexanol and hexanal. The selectivity of the catalyst of the present invention is exceptional for this type of reaction, while the activity is high as well, resulting in greater efficiency in producing such alcohols and aldehydes. In the prior art, such alcohols are produced in rather minor amounts. With the present catalyst, it is possible to obtain such alcohols, e.g., n-hexanol and isohexanol as the major product.

Hydroformylation can generally be affected by contacting the olefinically-unsaturated feed with hydrogen and carbon monoxide under pressure and in the presence of the catalyst at a temperature of from about 80° C. to 200° C., preferably about 100° C. to 150° C. These temperatures can be about 40° to 60° C. lower than those normally associated with the hydroformylation of low molecular olefins at a given conversion level, although the reaction can be run at a temperature of up to about 300° C. Elevated temperatures ordinarily can be maintained by the heat of reaction without external heating means. In many cases, it may be necessary to control the temperature by cooling, as for example, by circulating and cooling through heat exchange tubes in the reactor. Pressures of up to about 3000 or more psig., preferably about 500 to 2000 psig. or even 700 to 1800 psig. are suitable with the catalyst composition in the present invention. The pressures used in this process with this particular catalyst can also be lower than those normally associated with hydroformylation reaction at a given conversion level. The amount of catalyst composition used in the reaction is that amount sufficient to enhance the hydroformylation or hydroxyformylation of the feed and often the olefin feed contacts the catalyst at the rate of about 1 to 20, preferably about 1 to 10 WHSV (weight per weight of catalyst per hour). The process is applicable to continuous processing, e.g. with a catalyst slurry or a fixed bed, as well as batch processes. The hydrogen and carbon monoxide are preferably introduced into the reactor as a premixed gas in the molar ratio of hydrogen to carbon monoxide of from about 1.1 to 1 to 5 to 1, preferably from about 1.2 to 1 to 3.5 to 1. The catalyst system can be readily regenerated by the addition of fresh Group VA electron donor ligand to the deactivated catalyst.

DESCRIPTION OF SOME PREFERRED EMBODIMENTS

The preparation of an acidic silica-alumina support of this invention is illustrated by Examples I–III, and the support contains a separate phase of alumina.

EXAMPLE I

An alumina hydrogel is prepared as follows:
In a tank containing 5700 gallons of water at 85° F., are dissolved 300 lbs. of soda ash. When the soda ash has been dissolved, 180 gallons of a 39% concentration aqueous sodium aluminate solution are pumped into the tank in about a 15-minute period. The contents of the tank are at about 84° F. 600 gallons of aqueous aluminum sulfate of 7.8% concentration, as $Al_2O_3$, are added to the admixture over an 80-minute period with water of dilution in conjunction with, and in addition thereto, diluting the reaction mass at a rate of 25 gallons per minute.

The pH of the resulting aqueous reaction mass is adjusted to 8.0 with about 75 gallons of 39% concentration aqueous sodium aluminate solution which, while being added, is also diluted continuously with water at a rate of 35 gallons per minute over a 7 ½ minute addition period. The contents of the tank are heated to about 100° F., and pumped to storage.

The precipitated, hydrated alumina is thereafter filtered on a large gel filter. The filtered product is partially purified by a one-cycle, water-wash on the filter on which it is collected. This filter is a string vacuum type drum filter with a built-in water spray nozzle directed toward the filter drum. Material on the drum is contacted with water as the drum rotates past the nozzle. After washing, the wet alumina hydrogel is stripped from the drum. This hydrogel analyzes about 50% boehmite having a crystallite size of about 35 A, and 50% amorphous hydrous alumina as determined by X-ray diffraction on dried samples.

EXAMPLE II

A silica-alumina hydrogel is prepared by the following technique:
To a batch tank is added 4,275 gallons of water preheated to 90° F., and 865 gallons of sodium silicate solution (28.8 weight percent $SiO_2$, 40–41.5 Baume at 68° F., and $Na_2O:SiO_2$ ratio of 1:3.2) is added. The batch is stirred for 5 minutes. The concentration of the sodium silicate, as $SiO_2$, in the batch is 6.3 weight percent.

With the batch at 90° F., 302 gallons of 34.5 weight percent sulfuric acid solution at 182° F. are added over a period of 45 minutes. The gel forms about 35 minutes after acid addition is begun. Then the pH is adjusted to 8.0–8.5. The batch is agitated for 10 minutes.

Then 715 gallons of alum (7.8 weight percent, as $Al_2O_3$) is added to the gel over a period of about 36 minutes. The batch is agitated for an additional 5 minutes whereupon 205 gallons of sodium aluminate solution (24.4 weight percent as $Al_2O_3$) diluted in 1080 gallons of water is added over a period of 17 minutes. After all the sodium aluminate is added, the pH is checked. It should be between 5.0 and 5.2. The alumina content of the silica-alumina hydrogel is 30–31%.

EXAMPLE III

The silica-alumina hydrogel product of Example II and 1740 gallons of the alumina hydrogel filter cake of Example I are mixed together for 1 hour. The finished batch has a pH of 5.5 to 5.6 and a temperature of about 110° F. The aqueous gel mixture is then pumped to a dewatering filter and the filter cake from said dewatering filter and a portion of aqueous gel are blended to give a gel slurry of about 14 weight percent solids. A portion of this hydrogel mixture was slurried, as a thick flowable paste, with a "Lightnin" stirrer fitted with a cage-beater and a propellor, for about 10 minutes to give a thorough dispersion. The product was stirred 1 minute at 14,500 rpm. in a Waring Blender and dried in a laboratory spray-drier. The spray-dried material was washed with water to acceptable impurity levels and dried at 230° F. The washed and dried material analyzed 0.08% $SO_4$ and less than 25 ppm $Na_2O$. The dried material as such was used as the catalyst support, as were extruded forms thereof and tablets (pellets) having diameters of about ⅛ inch and lengths of about ⅛ to ½ inch. Before use, the catalyst support was calcined in a muffle furnace by raising the temperature of 300° F. per hour until 1350° F. was reached. This temperature was then held for three hours. The calcined particles had a surface area of about 320 to 340 square meters per gram.

EXAMPLE IV

The effect of a promotor, palladium acetylacetonate, on the temperature initiating the hydroformylation reaction of propylene in the presence of the supported cobalt complex catalyst was investigated. Cobalt naphthenate (3.0 m moles) and 0.2 m moles palladium acetylacetonate were dissolved in 75 ml o-xylene in a flask. The resulting solution was quantitatively transfered to a 300 cc. autoclave. Microspheroids of the support of Example III (10.0 g.) was added to the solution. The reactor was tightly closed, purged with hydrogen, and pressurized with a premixed gas (1:1 $H_2/CO$). The system was allowed to react under 900 psig. at 165° C for about ½ hour. After the reactor was allowed to cool overnight, the pressure was released and tri-n-butylphosphine (9.0 m moles) and 20 g. of propylene were injected into the reactor. The reactor was again pressured to 850 psig., using the premixed gas. The rate of heating of the reactor by an external heater was adjusted to increase the reaction temperature from room temperature to 100° C. within 180 minutes. The initial pressure drop was noticed under 1290 psig at 112° C. after about a 3-hour reaction. Thus, the temperature initiating the reaction must be lower than 112° C. under the aforementioned conditions. The reactor was kept at 112°–118° C. for 2 hours. The pressure dropped from 1290 psig. to 1200 psig. during this period. The temperature was then increased and maintained in the range of 120°–145° C. for an additional 2 ½ hours. During this period, the pressure of the reactor dropped to 700 psig. within 2 hours, and the reactor was then repressured to 850 psig. twice with the same premixed gas to keep the pressure of the reactor in the range of 850–700 psig. for ½ hour. A red-orange reaction mixture was filtered out of the reactor. The solid catalyst was washed with fresh portions of o-xylene. The catalyst was saved for four more consecutive batch runs. The results obtained in these runs are tabulated in Tables I and II.

In the first run, cobalt and palladium complexes were added in a large excess to saturate the supporting base with the cobalt catalyst species and the promoter. The cobalt and palladium supported on the base from the first run must be much less than the original amounts present in the liquid phase. It is quite simple to support these components quantitatively on the base by adding sufficient amount of the base to the soluble catalyst species. The second run was started by introducing 20 g. of propylene in 50 ml. o-xylene to the solid catalyst aged for 24 hours from the first run. The pressure of the reactor at this stage was 200 psig. and was raised to 800 psig. with a premixed gas (1:1 $H_2/CO$), and then to 1200 psig. with $H_2$. The reactor was slowly heated to 100° C. from room temperature (10° C.) in a 2 ½ hour period. The initial pressure drop was observed under 1660 psig. at 100° C. The pressure dropped from 1685 psig. to 1550 psig. (at the temperature range 100°–124° C.) within 3 ½ hours. The reaction was allowed to proceed for an additional 2 hours at a little higher temperature range (124°–146° C.). The pressure of the reactor dropped to 800 psig. at this stage. A yellowish reaction mixture, indicating that no catalyst leaches away from the supporting base, was discharged from the reactor. Analysis of the two reaction mixtures discharged from the first and second runs showed that the product distributions are quite similar in both runs. In the first run, the propylene feed was reacted in 23% conversion to give 24.4% isobutanal, 60.2% n-butanal, 2.0% isobutanol, 8.9% n-butanol and 4.6% unidentified products; in the second run, the conversion of propylene was 21% and the product distribution was 14.6% isobutanal, 55.4% n-butanal, 3.7% isobutanol, 16.6% n-butanol, 0.2% 2-ethylhexanol and 10.4% unidentified products. It is obvious from these results that the cobalt carbonyl catalyst and palladium promoter are simultaneously supported on the same base and that the resulting supported solid catalyst exhibits an improved catalytic behavior. The co-supported solid catalyst (comprising cobalt and palladium) was capable of lowering the temperature required to initiate the hydroformylation of propylene by 40°–60° C. than the catalyst without the promoter (see Example V).

Three more runs were made with the same catalyst in the presence of alkylamines. Details of these runs are tabulated in Table I and II. Triethyl- and tributylamine were used in these reactions. The level of catalytic activity based on the apparent conversion of propylene was maintained well through these runs, and showed an increase in catalytic activity in the presence of amines. In the last run, 20 g. of propylene was reacted in 50% conversion to yield 30.9% isobutanol, 56.6% n-butanal, 1.6% isobutanol, 3.8% n-butanol and 7.2% unknown products.

EXAMPLE V

A similar reaction was repeated in the presence of the cobalt supported catalyst without the palladium promoter as described in the preceding example. The results are summarized in Tables III and IV and can be compared to these results obtained from the preceding runs with a promoter.

TABLE I

| Ex. No. | Run No. | Co* | Pd* | Bu₃P | Cat. Base | Solvent ml | | Cat. Aged | Press. Temp. (to initiate reaction) | | Pressure Range | Temperature Range | Reaction Time | H₂/CO |
|---|---|---|---|---|---|---|---|---|---|---|---|---|---|---|
| | | | | | | tri-butyl-amine | tri-ethyl-amine o-xy-lene | psig | °C. | psig | °C. | hr. | | |
| | | m moles | | | g. | | | | | | | | | |
| IV | 1st | 3.0 | 0.2 | 9.0 | 10.0 | | 75 | — | 1290 | 112 | 1290–700 | 112–145 | 4 | 1 |
| | 2nd | <3.0 | <0.2 | <9.0 | 10.0 | | 50 | 24 | 1600 | 100 | 1685–800 | 110–146 | 5½ | 2 |
| | 3rd | | | <9.0 | 10.0 | | 5⁽¹⁾ 50 | 48 | 1520 | 120 | 1520–100 | 120–144 | 2¼ | 2 |
| | 4th | <3.0 | <0.2 | <9.0 | 10.0 | 5⁽¹⁾ | 50 | 56 | — | — | 1860–1240 | 192–198 | ⅔ | 2 |
| | 5th | <3.0 | <0.2 | <9.0 | 10.0 | | 5⁽¹⁾ 50 | 73 | — | — | 1905–1225 | 141–189 | ~10 | 2 |

*Co was added as Co-naphthenate; Pd was added as Pd-acetylace-tonate.
⁽¹⁾5 mls of amine were used.

TABLE II

| Ex. No. | Run No. | Feed g | alc. & ald. | Conversion | iC₄—Al | n-C₄—Al | iC₄—OH | n-C₄—OH | Unknown | 2ETC₆—OH |
|---|---|---|---|---|---|---|---|---|---|---|
| | | | % | % | Wt. % | | | | | |
| IV | 1st | C₃ = 20 | 95 | 23 | 24.4 | 60.2 | 2.0 | 8.9 | 4.6 | — |
| | 2nd | C₃ = 20 | 85 | 21 | 14.6 | 55.4 | 3.7 | 16.6 | 10.4 | 0.2 |
| | 3rd | C₃ = 20 | 90 | 30 | 38.7 | 39.2 | 2.5 | 11.9 | 7.7 | — |
| | 4th | C₃ = 20 | 99 | 14 | 25.6 | 59.6 | 2.5 | 11.2 | 1.1 | — |
| | 5th | C₃ = 20 | — | 50 | 30.9 | 56.6 | 1.6 | 3.8 | 7.2 | — |

TABLE III

| Ex. No. | Run No. | Co* | Pd | Bu₃P | Cat. Base | Solvent | Cat. Aged | Press. Temp. (to initiate reaction) | | Pressure | Temperature | Reaction Time | H₂/CO |
|---|---|---|---|---|---|---|---|---|---|---|---|---|---|
| | | m moles | | | g. | ml C₁₀—OH | hr. | psig | °C. | | | | |
| V | 1st | 3.0 | 0 | 9.0 | 10.0 | 70 | — | 1475 | 148 | 1475–1000 | 148–156 | ⅔ | 1 |
| | 2nd | 3.0 | 0 | 9.0 | 10.0 | 50 | 2½ | 1600 | 150 | 1600–1010 | 150–163 | 5/6 | 1 |
| | 3rd | 3.0 | 0 | 9.0 | 10.0 | 50 | 22 | 1840 | 145 | 1840–1425 | 145–161 | 1⅓ | 1 |
| | 4th | 3.0 | 0 | 9.0 | 10.0 | 50 | 46 | 1625 | 141 | 1625–960 | 141–177 | 1½ | 1 |

*Co was added as Co-naphthenate;

TABLE IV

| Ex. No. | Run No. | Feed g | Select to alc. & ald. | Conversion | iC₄—Al | n-C₄—Al | iC₄—OH | n-C₄—OH | Unknown** | 2EtC₆—OH |
|---|---|---|---|---|---|---|---|---|---|---|
| | | | | % | | | | | | |
| V | 1st | C₃ = 20 | 88 | 13 | 16.3 | 47.0 | 5.0 | 13.4 | 13.8 | 4.2 |
| | 2nd | C₃ = 20 | 85 | 31 | 13.8 | 39.4 | 5.3 | 17.3 | 13.4 | 10.8 |
| | 3rd | C₃ = 25 | 78 | 32 | 12.6 | 31.1 | 4.3 | 16.0 | 22.7 | 13.4 |
| | 4th | C₃ = 20 | 70 | 45 | 10.1 | 26.9 | 5.0 | 16.4 | 26.5 | 15.1 |

**Unknown + heavy products.

I claim:

1. In a process for the hydroformylation of olefin hydrocarbons of 2 to about 16 carbon atoms in contact with a catalyst composition comprises a minor, catalytically effective amount of cobalt modified by a smaller amount of a platinum group metal, and further modified by a triorganophosphine electron donor ligand, each ligand having three hydrocarbon groups devoid of olefinic and acetylenic unsaturation and selected from the group consisting of lower alkyl, monocyclic aryl, alkylmonocyclicaryl, monocyclicaraalkyl, and cycloalkyl groups, said hydroformylation being conducted at a temperature of from about 60° to 400° C. and at a pressure from about 500 psig to a 3000 psig and an hourly space velocity of weight of olefin per weight of catalyst of from about 1 to to about 20, the hydrogen to carbon monoxide mole ratio being from about 1:1 to about 5:1, the improvement which comprises supporting said cobalt and said platinum group metal components upon a solid-acidic support containing a separate phase of alumina, the total catalyst composition containing 0.01 to 0.03 weight per cent of noble metal of the group consisting of platinum, palladium, rhodium, osmium, iridium, ruthenium, and mixtures thereof, and 0.2 to 0.6 weight per cent cobalt, said support being calcined and comprising 45 to 95 weight per cent amorphous acidic calcined silica-alumina having a Cat-A activity of about 30, and about 5–55 weight per cent separate phase alumina, the total alumina content of said support having about 20 to 70 weight per cent, said separate phase alumina resulting from the calcination of a mixture of amorphous hydrous alumina and alumina monohydrate; said support containing less than 1.5 weight per cent sodium, said support being prepared by mixing together a separate, phase alumina hydrogel with a silica-alumina hydrogel, dewatering the mixture to provide a gel slurry of about 14 weight per cent solids, spray-drying said slurry, washing the spray-dried material, pelleting the washed material, and calcining the pellets at about 1350° F. for about three hours to provide calcined particles.

2. The process of claim 1 wherein the hydroformylation is conducted at a temperature of from about 100° to 200° C.

3. The process of claim 1 wherein said olefin is propylene.

4. The process of claim 1 wherein the mole ratio of ligand to cobalt is from about 1.5:1 to 3:1.

5. The process of claim 1 wherein a solution of cobalt acetylacetonate is employed to impregnate the support with from 0.2 to 0.6 weight per cent cobalt into the catalyst composition.

* * * * *